US007135100B1

(12) United States Patent
Lau et al.

(10) Patent No.: US 7,135,100 B1
(45) Date of Patent: Nov. 14, 2006

(54) AMPEROMETRIC SENSOR

(75) Inventors: Kim King Tong Lau, London (GB); Jonathan Mark Slater, London (GB)

(73) Assignee: Drew Scientific Ventures LLC, Dallas, TX (US)

( * ) Notice: Subject to any disclaimer, the term of this patent is extended or adjusted under 35 U.S.C. 154(b) by 252 days.

(21) Appl. No.: 10/019,220

(22) PCT Filed: Jun. 29, 2000

(86) PCT No.: PCT/GB00/02504

§ 371 (c)(1),
(2), (4) Date: May 16, 2002

(87) PCT Pub. No.: WO01/00865

PCT Pub. Date: Jan. 4, 2001

(30) Foreign Application Priority Data

Jun. 29, 1999 (GB) ................... 9915181.3

(51) Int. Cl.
*G01N 27/327* (2006.01)
*G01N 27/333* (2006.01)
(52) U.S. Cl. .................. 204/403.14; 204/403.11; 204/416
(58) Field of Classification Search ........ 204/403.04, 204/403.09, 403.1, 403.11, 403.14, 403.12, 204/416–418; 205/782
See application file for complete search history.

(56) References Cited

U.S. PATENT DOCUMENTS

| 4,224,125 A * | 9/1980 | Nakamura et al. ..... 204/403.09 |
| 4,552,840 A * | 11/1985 | Riffer .......................... 205/778 |
| 4,711,245 A | 12/1987 | Hill .......................... 204/403.1 |
| 4,929,545 A | 5/1990 | Freittag ...................... 435/11 |
| 5,380,422 A * | 1/1995 | Negishi et al. ......... 204/403.04 |
| 5,624,537 A * | 4/1997 | Turner et al. ............ 422/82.01 |

FOREIGN PATENT DOCUMENTS

| EP | 0 400 918 A | 12/1990 |
| EP | 0400918 A1 * | 12/1990 |
| JP | 04-70558 A * | 3/1992 |
| JP | 07-103933 A * | 4/1995 |
| JP | 09-101281 A * | 4/1997 |
| WO | WO 95 21934 A | 8/1995 |

OTHER PUBLICATIONS

CAPLUS abstract of Chen et al. ("Redox electrode for monitoring oxidase-catalyzed reactions," Clinica Chimica Acta (1990), 193(3), 187-92).*
CAPLUS abstract of Ikeda et al. ("an efficient method for entrapping ionic mediators in the enzyme layer of mediated amperometric biosensors," agricultural and Biological Chemistry (1988), 52(12), 3187-8).*
CAPLUS abstract of Yao et al. ("Flow injection analysis for uric acid by the combined use of an immobilized uricase reactor and a peroxidase electrode," Nippon Kagaku Kaishi (1985), (2), 189-92).*
CAPLUS abstract of Zhdanov et al. ("Amperometric titration of hydrogen peroxide by solutions of some oxidizing agents in an apparatus with a rotating platinum electrode," Uzbekskii Khimicheskii Zhurnal (1968), 12(2), 16-18).*

(Continued)

*Primary Examiner*—Alex Noguerola
(74) *Attorney, Agent, or Firm*—Duane Morris LLP

(57) ABSTRACT

An amperometric sensor suitable for determining the concentration of hydrogen peroxide in a sample, said sensor comprising a ferricyanide compound which, in reduced form, functions as a mediator specific to hydrogen peroxide.

25 Claims, 5 Drawing Sheets

OTHER PUBLICATIONS

Figure 1:
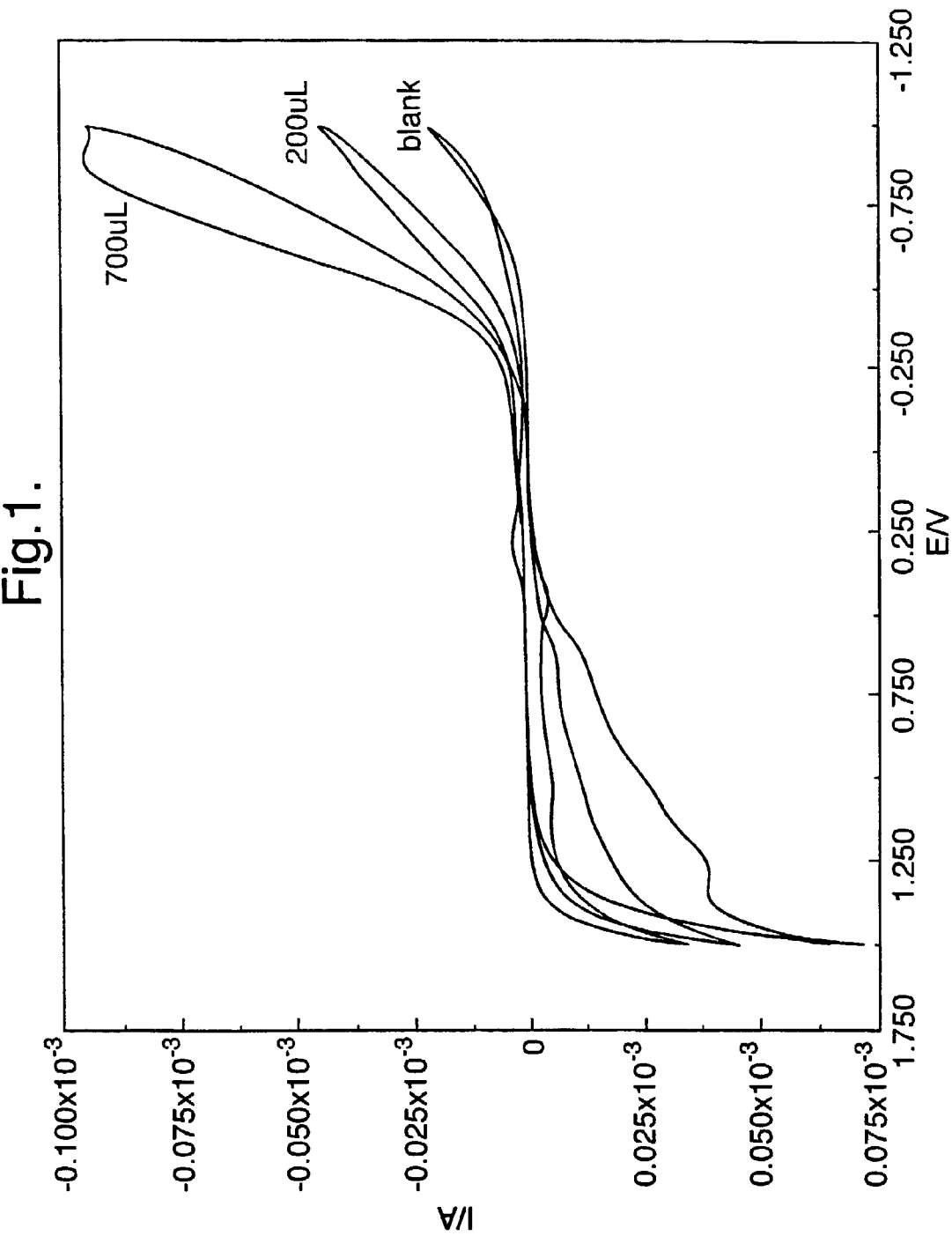

CAPLUS abstract of Zhdanov et al. ("amperometric titration of potassium ferricyanide with hydrogen peroxide on an apparatus with a rotating platinum electrode," Uzbekskii Khimicheskii Zhurnal (1967), 11(4), 17-19).*

CAPLUS abstract of Blaedel et al. ("Continuous analysis by the amperometirc measurement of reaction rate," Anal. Chem. (1964), 36(2), 343-7).*

Svitel et al. ("Composite Biosensor for Sulfite Assay: Use of Water-Insoluble Hexacyanoferrate(III) Salts as Electron-Transfer Mediators," Electroanalysis 1998, 10, No. 9). published in Jul. of 1998.*

CAPLUS abstract of Valdes et al. (amperometric determination of sulfite and hydrogen peroxide in aqueous solution by flow injeciton analysis with immobilized sulfite oxidase, Ingeniera y Ciencia Quimica (1995), 15(2), 35-8).*

CAPLUS abstract for Baeza et al. ("The hydrogen ion dependence of amperometric detection of H2O2 and hexacyanoferrate ions and the pH profiles of immobilized enzyme preparations," Quimica Analitica (Barcelona, Spain) (1993), 12(1), 12-17).*

CAPLUS abstract of Shiiki et al. (JP 04070558 A2).*

Alcohol dehydrogenase reaction pathway downloaded from www.worthington-biochem.com/ADH/default.html.*

CAPLUS abstract of Tatsuma et al. ("Oxidase/peroxidase bilayer-modified electrodes as sensors for lactate, pyruvate, cholesterol and uric acid," Analytica Chimica Acta (1991), 242(1), 85-9).*

Data File: Ion exchange chromatography, Sephadex ion exchange media by Amersham Biosciences.*

Ikeda et al. ("An efficient method for entrapping ionic mediators in the enzyme layer of mediated amperometric biosensors," Agricultural and Biological Chemistry (1988), 52(12), 3187-8).*

Yao et al. ("Flow injection analysis for uric acid by the combined use of an immobilized uricase reactor and a peroxidase electrode," Nippon Kagaku Kaishi (1985), (2), 189-92).*

Blaedel et al., ("Continuous analysis by the amperometric measurement of reaction rate," Anal. Chem. (1964), 36(2), 343-7).*

English language translation of JP 04-070558, Shiiki et al.*

JPO English language computer translation of Goto et al. (JP 09-101281 A) Apr. 15, 1997.*

JPO English language computer translation of Yamamoto et al. (JP 07-103933 A) Apr. 21, 1995.*

Product description 216534 for Amberlite IR120 hydrogen form from www.sigmaaldrich.com downloaded Feb. 18, 2006.*

ACS File Registry entriy for polylysine. Downloaded on Feb. 18, 2006 from ACS on STN.*

ACS File Registry entriy for polyornithine. Downloaded on Feb. 18, 2006 from ACS on STN.*

Database Chemabs: Shiiki, Mikio et al, "Ethanol sensor using alcohol dehydrogenase" & JP 04 070558, Mar. 5, 1992.

Database Chemabs: Svitel, Juraj et al, "Composite biosensor for sulfite assay. Use of water-insoluble hexacyanoferrate (III) salts as electron-transfer mediators", Electroanalysis (1998), 591-596.

Database Chemabs: Schuberg, Floria et al, "Mediated amperometric enzyme electrode incorporating peroxidase for the determination of hydrogen peroxide in organic solvents", Anal. Chim Acta (1991), 245(2), 133-8.

\* cited by examiner

AMPEROMETRIC SENSOR

This application is the U.S. national phase of international application PCT/GB00/02504 filed Jun. 29, 2000 which designated the U.S.

In general terms the present invention relates to the determination of the concentration of an analyte in a sample. More specifically, the invention relates to an amperometric sensor, to its use, to cartridges for the sensor and to redox mediator compounds for use in the sensor.

A number of electrochemical sensors (or biosensors) have been proposed previously. For example, U.S. Pat. No. 5,288,636 describes a sensor useful for determining glucose concentration in a sample and relies on the reaction between the enzyme glucose oxidase and glucose with the mediator potassium ferricyanide to produce a ferrocyanide which is then electro-oxidised to produce a measurable current that is representative of the concentration of glucose present.

The reactions involved can be summarised as follows:

1. $GOD_{OX}$ + glucose $\longrightarrow$ gluconic acid + $GOD_{RED}$
2. $GOD_{RED}$ + $M_{OX}$ $\longrightarrow$ $GOD_{OX}$ + $M_{RED}$
3. $M_{RED}$ $\longrightarrow$ $M_{OX}$ + $e^-$ [Signal]

$GOD_{OX}$—oxidised form of glucose oxidase
$GOD_{RED}$—reduced form of glucose oxidase
$M_{OX}$—oxidised form of mediator (ferricyanide)
$M_{RED}$—reduced form of mediator (ferrocyanide)

In step 1 the enzyme oxidizes the glucose and is itself reduced. In step 2 the reduced form of the enzyme reacts with the oxidised form of the mediator to produce the reduced form of the mediator. In step 3 the oxidised form of the mediator is regenerated by electro-oxidation. A measurable current/signal is generated. Thus, this type of sensor depends on reaction between the mediator and enzyme.

U.S. Pat. No. 4,711,245 also describes a sensor for determining glucose concentration. The sensor relies on a reaction involving the enzyme glucose oxidase, glucose and the oxidised form of a substituted ferrocene. The ferrocene is reduced and then re-oxidised to produce an easily measurable current.

There are several disadvantages associated with known sensors. Firstly, the mediators used can be unstable and tend to undergo autoxidation Secondly, in known sensors a potential is applied between electrodes in order to oxidise the reduced form of the mediator. At potentials which are sufficient to achieve this interferants present in the system, for example ascorbates, urate and paracetamol, tend to be oxidised. Both of these effects lead to inaccurate measurement of analyte concentration. In the latter case, the analyte concentration is typically overestimated due to a non-specific oxidation current. With respect to this particular problem, it would be advantageous to use the sensor at assay potentials more negative than +100 mV (Ag/Ag Cl) to avoid measuring signal due to common interferants.

The present invention solves these problems by use of a sensor which relies on the reaction between a mediator compound and hydrogen peroxide. The hydrogen peroxide may be the analyte it is desired to assay or it may be the product of an enzyme-analyte reaction. An important feature of the sensor is that in the reduced form the mediator can be detected electrochemically at a potential of about −400 mV (Ag/AgCl). At such a potential, oxidation of common interferants is avoided.

Accordingly, the present invention provides an amperometric sensor suitable for determining the concentration of hydrogen peroxide in a sample, said sensor comprising a ferricyanide compound which, in reduced form, functions as a mediator selective to hydrogen peroxide.

The sensors of the invention may, of course, be used to determine the concentration of hydrogen peroxide in a sample. However, as is evident from the reaction scheme above, hydrogen peroxide may be generated as a product of an analyte-enzyme reaction, such as between glucose and glucose oxidase. The sensors can therefore be used to determine the concentration of such analytes. In this embodiment the sensor further comprises an enzyme which is capable of reacting with the analyte in a sample to produce hydrogen peroxide. Typically, the enzyme will be an oxidase type enzyme. For example, in a sensor for determining the concentration of glucose in a sample, the enzyme may be glucose oxidase. The reaction between the enzyme and analyte yields hydrogen peroxide in the presence of oxygen, and the concentration of the hydrogen peroxide can be determined using the sensor and correlated to a corresponding glucose concentration Other analytes which may be determined using the sensor of the present invention include chloresterol, pyruvate, bilirubin, alcohol and lactate; U.S. Pat. No. 5,288,636 gives details of the relevant enzymes and mediators.

Further analytes may be measured if suitable additional enzymes and/or mediators are included in the sensor. Examples of this include triglycerides and HDL cholesterol. Of course the sensors should be constructed so that the final product of the enzyme reactions detected by the ferricyanide mediator, is hydrogen peroxide.

Herein the term "mediator" means a compound which is capable of undergoing an electrochemical, reversible oxidation-reduction reaction.

The mediator used in the present invention is a ferricyanide compound which in reduced form is selective for hydrogen peroxide, i.e. which is oxidised on reaction with hydrogen peroxide. Examples of suitable compounds include those of general formula (I)

$$X_3Fe(CN)_6 \qquad (I)$$

in which the groups X are the same or different and each is a non-metallic ion or any other organic or inorganic species provided that at least one group X is a non-metallic ion and provided that the compound of formula (I) has satisfactory solubility in water and common organic solvents.

Solubility of the compound of Formula (I) is an important factor in the proper functioning of the sensor. Low solubility in water and aqueous phases is helpful in providing stability and conveniently the compound of Formula (I) should have a solubility of from 2000 mg/L to 20,000 mg/L in pure water. Solubility in common organic solvents is desirable to facilitate fabrication of the sensors and conveniently the compound of Formula (I) will have a solubility of at least 20,000 mg/L and preferably higher, in at least one of methanol, ethanol, propanol, other lower alkanols, chloroform, dichloromethane or other chlorinated alkanes and acetone and other low molecular weight ketone and ether solvents.

Groups X may be selected from any known organic or inorganic groups and ions subject to the above restrictions. Examples of groups X include all metal ions, especially all monovalent metal ions and particularly all alkali metal ions such as sodium and potassium ions. Other suitable groups X include quaternary ammonium ions and quaternary phosphonium ions.

Preferably the mediator is specific to hydrogen peroxide, i.e. under the conditions of the analysis, the mediator only provides electrons for hydrogen peroxide. In practice it is likely that this will be the case when operating at the preferred potential (see below). However specificity is not essential and the system may be operated satisfactorily provided that the mediator is selective for hydrogen peroxide, i.e. under the conditions of the analysis the mediator tends to provide electrons to hydrogen peroxide in preference to any other electron acceptor available to the mediator.

In this formula X may be a quaternary ammonium ion, for instance of formula (II)

$$(R^1)(R^2)(R^3)(R^4)N^- \quad (II)$$

in which $R^1$ to $R^4$ are the same or different alkyl groups containing from 1 to 20 carbon atoms, provided that a least one of $R^1$ to $R^4$ contains at least 4 carbon atoms. Typically, $R^1$ to $R^4$ are selected from amongst alkyl groups containing from 4 to 20 carbon atoms, preferably from 4 to 16 carbon atoms. Conveniently the quaternary ammonium ion will have four identical alkyl groups in which case the alkyl groups are preferably selected from those of 5 to 11 carbon atoms. As an alternative the quaternary ammonium ions may conveniently have only one long chain alkyl group and three identical short chain alkyl groups such as methyl groups. In this case the long chain alkyl group is preferably selected from those of 6 to 20 carbon atoms.

The longer alkyl groups render the quaternary ammonium ions relatively insoluble which is an advantage in the present invention. It is preferred that the quaternary ammonium ions used have a solubility of not more than 100 mg.L$^{-1}$ in water at room temperature (20 C), more preferably not more than 10 mg.L$^{-1}$ and most preferably not more than 1 mg.L$^{-1}$. As specific examples of useful compounds there may be mentioned tetrahexyl-, hexyltrimethyl-, tetrakisdecyl-, tetradecyltrimethyl- and hexadecyltrimethylammonium ferricyanides.

In another embodiment of the invention, the group X may be a phosphonium ion, for example of formula $(R^5)(R^6)(R^7)(R^8) P^+$ in which $R^5$ to $R^8$ are the same or different alkyl groups containing from 1 to 20 carbon atoms, provided that at least one group $R^5$ to $R^8$ contains at least 4 carbon atoms.

In a further embodiment the group X may be a nitrogen-containing heterocyclic cation. The heterocyclic group may be saturated, unsaturated or aromatic. As an example, X as pyridinium may be mentioned.

The alkyl groups mentioned above may be straight or branched-chain. The alkyl and heterocyclic groups may be substituted by one or more substituents provided that these do not have a detrimental effect on the activity of the mediator compounds.

In a particular embodiment of the invention the ferricyanide anions $[Fe(CN)_6]^{3-}$ may be bound to a polymeric support via functional groups on the polymer. One class of such functional groups includes the quaternary ammonium ions

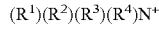

wherein one of $R^1$ to $R^4$ is the polymeric backbone and the other groups are as defined above. Another class of such functional groups includes the quaternary phosphonium ions

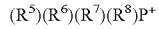

in which one of $R^5$ to $R^8$ is the polymeric backbone and the other groups are as defined above. A further class of such functional groups includes nitrogen-containing heterocyclic cations which may be saturated, unsaturated or aromatic such a pyridinium and where the heterocyclic moiety is bound to or forms part of the polymeric backbone.

Suitable polymers are well known to those skilled in the art and may be readily produced by conventional techniques. Derivatisation with suitable functional groups may be achieved, when necessary, by known methods.

In a preferred embodiment the polymers have gel-forming properties. This may be achieved using gel-forming blocks within the polymer coupled with functional group-bearing blocks or by forming random copolymers having gel-forming and functional moieties. Included within the gel forming polymers are functionalised polyacrylamides and polymers of a block structure such as

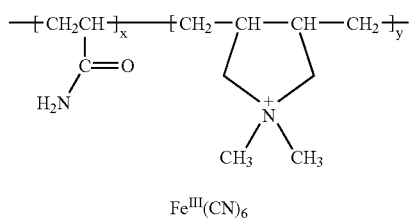

Polymers may be soluble in water or insoluble but preferably have a solubility less than 20,000 mg/L and preferably have film or gel-forming properties.

Some of the compounds useful as mediators are known and are commercially available. Alternatively, they may be made by the application or adaptation of known techniques. Certain of the mediator compounds are new however and these form another aspect of the present invention. Thus, the invention also provides novel ferricyanide compounds of the above formula in which at least one X is a quaternary ammonium ion having at least one $C_6$ to $C_{20}$ alkyl group other than tridodecylmethyl-, methyltrioctyl-, dihexadecyldimethyl-, didodecyldimethyl-, hexadecyltrimethyl and tetraoctylammonium ions.

These ferricyanide compounds may be prepared by methods described in Svitel, J. et al., Electroanalysis, 1998, 10, No. 9, pp 591–596, and modifications thereof, using appropriate quaternary ammonium halides and ferricyanide salts. In general, a quaternary ammonium halide such as the chloride or preferably the bromide, is reacted with a ferricyanide salt, preferably an alkali metal salt such as sodium or, more preferably, potassium ferricyanide. The reaction may be conducted under suitable conditions of temperature and pressure, such as at room temperature or elevated temperature up to the boiling point of the reaction mixture, and at atmospheric pressure, and for sufficient duration such as from a few minutes to a few hours, preferably at 80° C. for 2 hours, in the presence of a suitable solvent such as water.

The mediator compounds disclosed herein are useful in a variety of amperometric sensor devices and electrode configurations. The sensors may be based on a 2 or 3 electrode system and may be of the disposable (single use) or re-usable/semi-disposable type.

In its simplest form the sensor comprises two electrodes (working and counter) which in use are contacted with the sample being analysed. One electrode, the working electrode, is coated with the mediator compound. The mediator is sparingly soluble or insoluble in aqueous solution and may be applied to the electrode by deposition from a solution of the mediator in a readily evaporable organic liquid. When the sensor is being used to determine the concentration of an analyte such as glucose the mediator is coated with a suitable enzyme. The enzyme can be immobilised on the surface of the mediator by conventional techniques such as by use of a self-sustaining gel layer and/or by use of a retention layer which is permeable to the analyte. U.S. Pat. No. 4,711,245 describes in greater detail ways in which the mediator and, when used, enzyme may be fixed on the working electrode.

The electrode substrate is chosen from conventional materials such as carbon pellets, carbon inks, metallized carbon and metals (such as platinum or palladium), carbon rods, pencil leads and carbon rods loaded with metal powder.

Conventional electrode configurations which may be used include those disclosed in U.S. Pat. No. 4,711,245, U.S. Pat. No. 5,200,051 and U.S. Pat. No. 5,288,636, incorporated herein by reference.

The basic chemical and electrochemical transformations associated with the present invention are shown below with reference to the glucose/glucose oxidase system. Prior to introduction of the sample to be analysed a potential of about −400 mV (Ag/AgCl) is applied to the sensor electrode. This potential is sufficient to cause reduction of the mediator at the working electrode, i.e. conversion of the ferricyanide to the corresponding ferrocyanide. When the electrodes are contacted with the sample to be analysed the enzyme at the working electrode acts on the glucose resulting in the production of hydrogen peroxide. The reaction proceeds as shown in reaction scheme 4 below.

The hydrogen peroxide produced oxidises the reduced form of the mediator as follows:

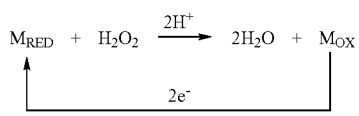

Instantaneously, under the applied potential, the oxidised form of the mediator at the working electrode is converted to the reduced form and a diffusion limited current generated. This current can be measured and correlated to the concentration of analyte in the sample.

At the electrode potential involved (−400 mV) there is no oxidation of interferants and the result obtained is an accurate reflection of the hydrogen peroxide concentration in the sample. The hydrogen peroxide concentration may be correlated to analyte concentration.

A diffusion limiting layer may be applied to the working electrode to extend the sensor to measurement of higher analyte concentrations. Examples of materials for use as the diffusion-limiting include Nafion™ and cellulose acetate.

It is envisaged that the sensors of the invention will find most practical utility in the measurement of glucose in blood samples, although they may also be used for other medical and non-medical applications, for example in the food industry.

BRIEF DESCRIPTION OF THE ACCOMPANYING DRAWINGS

FIG. 1 CV of hydrogen peroxide sensor showing the responses to background buffer solution and the increased responses when 200 uL and 700 uL 131 mM hydrogen peroxide were added into 4 ml buffer. The scan rate used was 50 mV/s.

Figure 2:
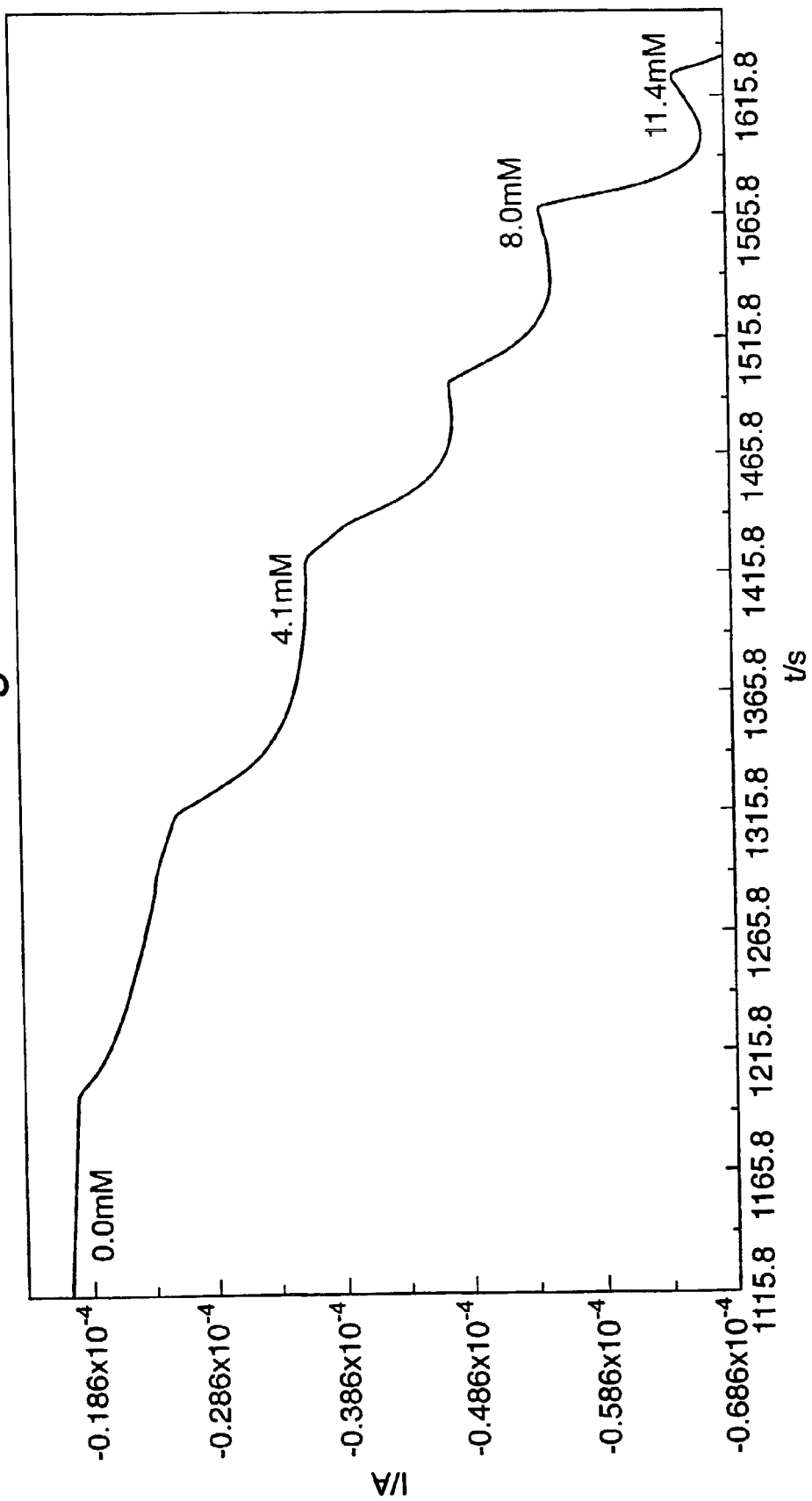

FIG. 2 The calibration trace for THAF mediated hydrogen peroxide sensor on addition of 88 mM hydrogen peroxide solution.

Figure 3:
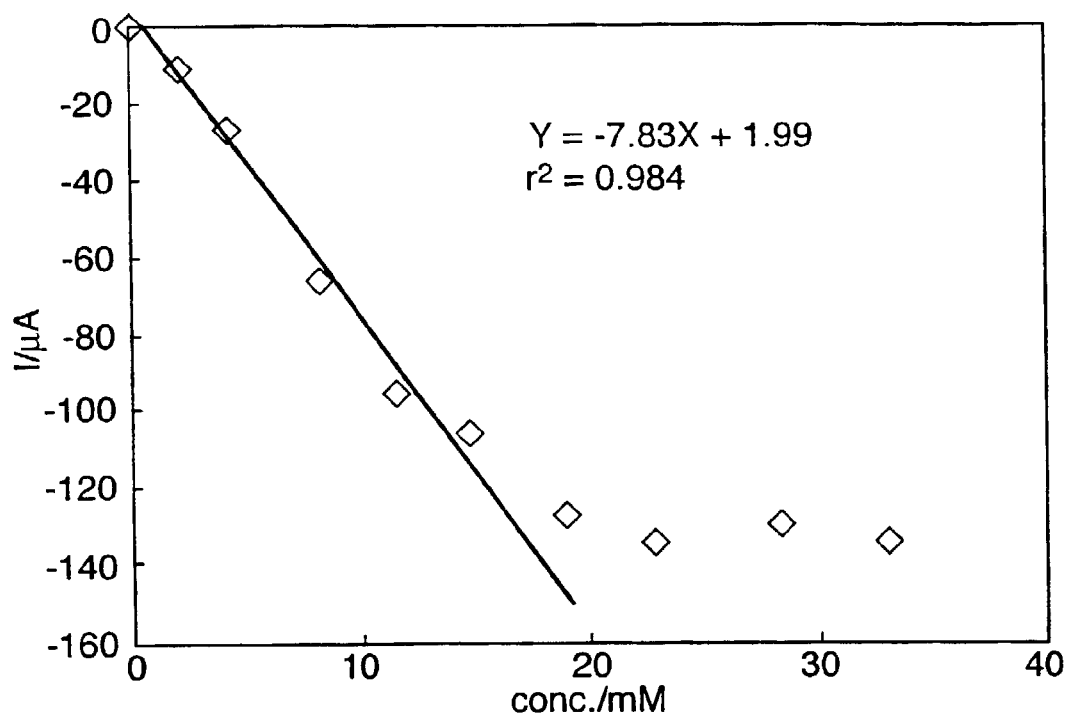

FIG. 3 Calibration plot for THAF mediated hydrogen peroxide sensor.

Figure 4:
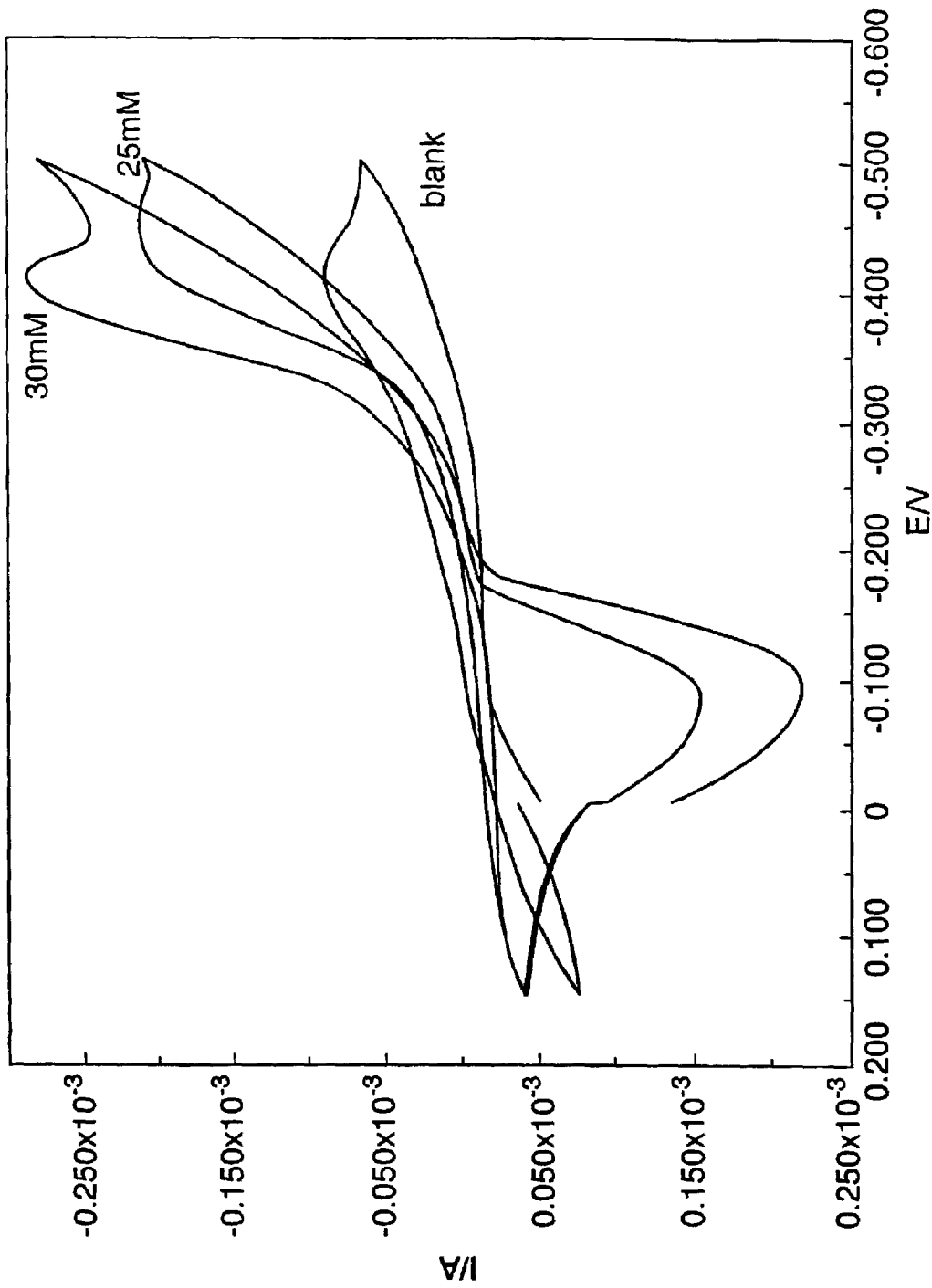

FIG. 4 CV of hydrogen peroxide sensor in the presence of glucose oxidase in solution showing the responses to different concentration of glucose. The scan rate used was 100 mV/s.

Figure 5:
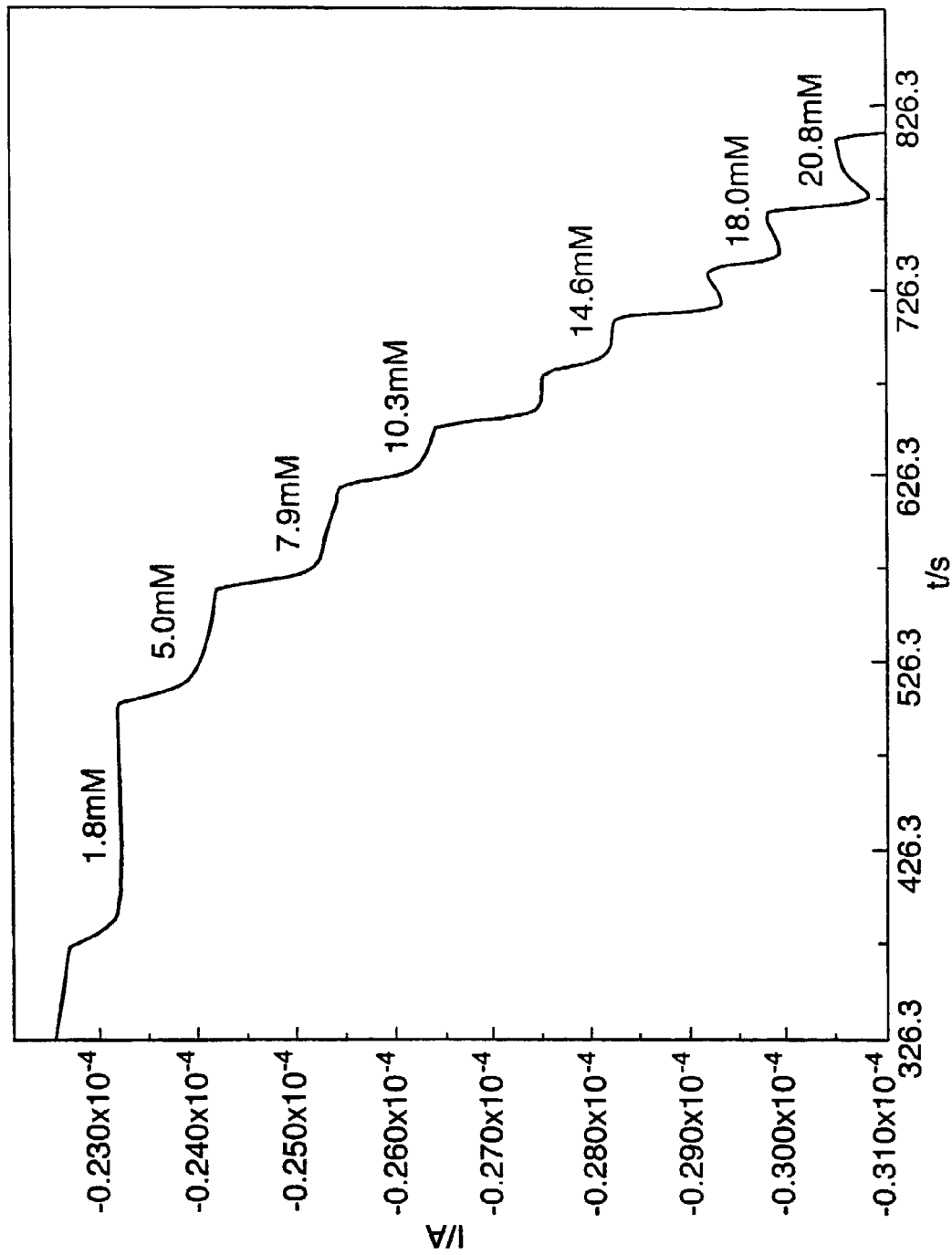

FIG. 5 The calibration trace for THAF mediated glucose sensor on standard addition of 50 mM glucose solution.

Figure 6:
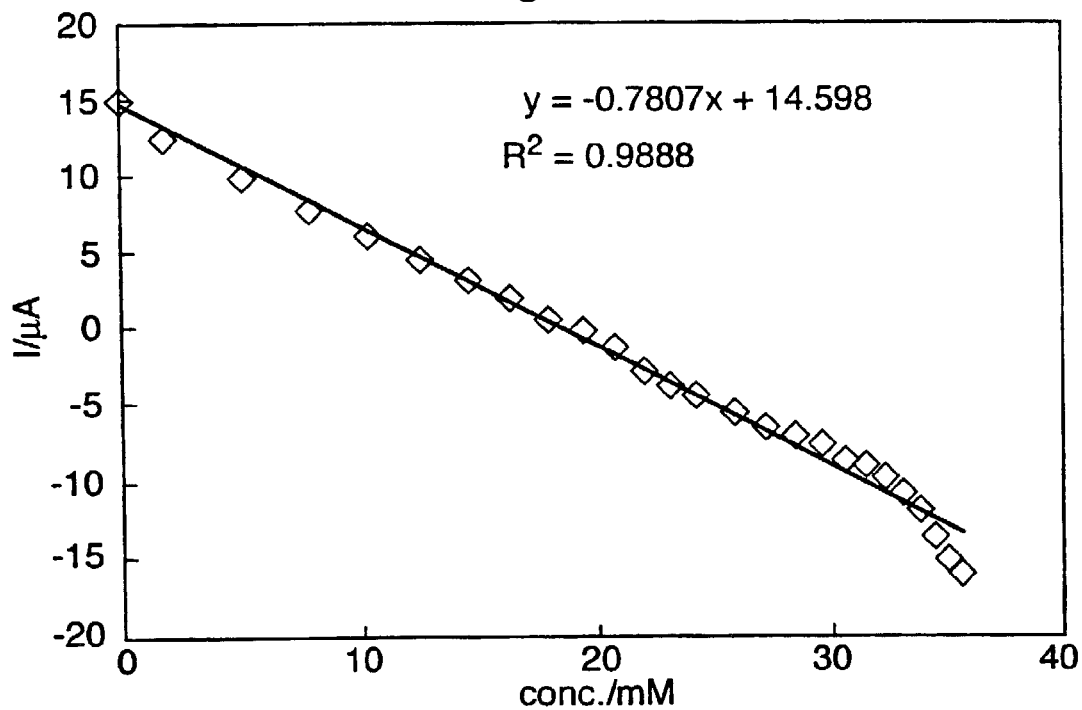

FIG. 6 Calibration plot for THAF mediated glucose sensor.

The following Examples illustrate the invention but are not intended to limit the scope of protection in any way.

EXAMPLES

Example 1

Synthesis of Mediator

Tetrahexylammonium ferricyanide (THAF) was prepared by adding an aqueous solution of potassium ferricyanide (Aldrich, Dorset, U.K.) (0.5 mmole 1.65 g) into a solution of tetrahexylammonium bromide (Aldrich, Dorset, U.K.) (1.5 mmole, 0.65 g) in 20 ml of distilled water and heating the mixture to 80° C. for 2 hr with vigorous stirring. A yellow coloured oil separated from the aqueous phase and was extracted with diethylether (3×10 ml). The ethereal extract was washed with distilled water (3×10 ml) and then dried over magnesium sulphate. Evaporating the solvent gave 1.1 g of yellow oil which solidified on standing.

Example 2

Electrode Construction

A silver loaded carbon pellet (Electrocarbon, Norfolk, U.K.) with a diameter of 2 mm and a length of 4 mm was fitted with a 1.8 mm internal diameter PVC rubber tubing section (4 mm in length) so that a recess of about 1 mm was left at one end. The other end of the pellet was fixed to a 5 cm long copper wire with silver expoxy glue as contact. The whole assembly was then fitted into another 4.5 cm long PVC tubing that fitted the electrode assembly tightly. The opening at the end of the tubing with exposed contact wire was then sealed with epoxy glue. The finished electrode assembly has an electrode area of 3.1 mm².

Example 3

Hydrogen Peroxide Sensor 1 uL of a 5.5% ethanolic solution of THAF (Example 1) was deposited onto the recess of the electrode prepared in Example 2 and allowed to dry for 3 minute. A 1 uL aliquot of Nafion™ solution (5% solution from Aldrich. Dorset, U.K.) in distilled water (9:1 mixture, final concentration 0.5%) was deposited on top of the ferricyanide layer to form a diffusion control membrane. The sensor was air-dried for at least 4 hr before use.

Example 4

Glucose Sensor

This biosensor was formed in a manner similar to that for the hydrogen peroxide sensor of Example 3 except that an enzyme layer was added in between the ferricyanide layer and the diffusion control layer. The enzyme layer used was made from two solutions:

Solution A: propanoic solution containing 2.2% THAF and 1.25% Nafion™.

Solution B: glucose oxidase solution (5 mg/ml about 200 U/mg) (Fluka, Dorset, U.K.).

A 1:1 mixture of solution A and solution B was prepared immediately before use and a total of 10 ul were deposited onto the THAF modified electrode in 2 uL aliquots. The sensor was dried in a gentle stream of air (about 30 min,) before a 1 uL aliquot of 0.5% Nafion™ solution in water was deposited over the enzyme layer. The sensor was air dried as before and kept dry at 4° C. overnight before use.

Example 5

Use of Hydrogen Peroxide Sensor

Cyclic voltammetry was used to show the activity of this sensor to hydrogen peroxide. A three electrode system was used with the sensor of Example 3 as the working electrode, a platinum electrode as the counter electrode and a silver-silver chloride electrode as the reference electrode. An AutoLab (Eco Chemie B.V.) electrochemical system was used for the measurements. Cyclic voltammetry at a scan rate of 50 m V/s and a scan range of −1.0V to 1.5V vs Ag—AgCl shows the increase in cathodic current when aliquots of 131 mM hydrogen peroxide (200 uL and 700 uL) in phosphate saline buffer solution were added into 4 ml of the same buffer solution at pH 7.4 (FIG. 1). The same cell set up was used for calibration of the sensor by amperometry; the current measured at the hydrogen peroxide sensor at an applied potential of −400 mV vs Ag—AgCl during an experiment where aliquots of 131 mM hydrogen peroxide in phosphate saline buffer were added to 4 ml of the same buffer was plotted (FIG. 2) A calibration plot (FIG. 3) resulting from the amperometry data shows a linear range from 0 to about 20 mM hydrogen peroxide.

Example 6

Use of Hydrogen Peroxide Sensor

Similar experiments to those of Example 5 were carried out using the hydrogen peroxide sensor of Example 3 in the same cell set up, except that the counter electrode used was a gold electrode. For all cases the buffer used for making up glucose solution and the blank (background) was phosphate saline buffer at pH 7.4. 200 uL of glucose oxidase solution (5 mg/mL, Fluka) was added into 4 mL buffer solution before the cyclic voltammetry studies. The scan rate for cyclic voltammetry measurement was 100 mV/s and the scan range used was 0.15V to −0.55V. The cyclic voltammagram (FIG. 4) obtained for different glucose concentrations shows cathodic currents at around −400 mV that indicate that the biosensor responded to hydrogen peroxide, which was produced by the action of the glucose oxidase on the glucose added and that the increase in cathodic current was concentration dependent.

Example 7

Use of Glucose Sensor

Similar experiments to those of Example 6 were carried out using the glucose sensor of Example 4 in the same cell set up. For all cases the buffer used for making up glucose solution and the blank (background) was phosphate saline buffer at pH 7.4. The current measured at the glucose sensor at an applied potential of −400 mV vs Ag—AgCl during an experiment where aliquots of 50 mM glucose in phosphate saline buffer were added to 4 ml of the same buffer shows a linear range from 0 to about 30 mM glucose (FIGS. 5 and 6).

The invention claimed is:

1. An amperometric sensor suitable for determining the concentration of hydrogen peroxide in a sample, said sensor comprising a ferricyanide compound which, in reduced form, functions as a mediator selective for hydrogen peroxide, wherein the ferricyanide compound is of general formula:

$$X_3Fe(CN)_6$$

wherein each X is a phosphonium ion of formula $(R^5)(R^6)(R^7)(R^8)P^+$ in which $R^5$ to $R^8$ are the same or different alkyl groups containing from 1 to 20 carbon atoms, provided that at least one group $R^5$ to $R^8$ contains at least 4 carbon atoms.

2. A sensor according to claim 1, further comprising an enzyme which is capable of reacting with an analyte in the sample to produce hydrogen peroxide.

3. A sensor according to claim 2, wherein the analyte is glucose and the enzyme is glucose oxidase.

4. A sensor according to claim 1, in which the ferricyanide compound is bound to a polymer.

5. A sensor according to claim 4, wherein the polymer is a polyacrylamide.

6. A sensor according to claim 4, wherein the ferricyanide compound is bound to the polymer via one of groups $R^5$ to $R^8$ of a quaternary phosphonium ion of formula $$(R^5)(R^6)(R^7)(R^8)P^+.$$

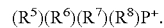

7. A sensor according to claim 1, wherein the ferricyanide compound has a solubility of from 2000 mg/L to 20,000 mg/L in pure water.

8. A sensor according to claim 7, wherein the ferricyanide compound is polypyridinium ammonium ferricyanide of poly(acrylamide-co-diethyldimethyl ammonium)ferricyanide.

9. A cartridge for an amperometric sensor suitable for measuring hydrogen peroxide in a sample, which cartridge comprises a ferricyanide compound as defined in claim 1.

10. A cartridge according to claim 9, further comprising an enzyme which is capable of reacting with an analyte in the sample to produce hydrogen peroxide.

11. A cartridge according to claim 10, wherein the enzyme is glucose oxidase.

12. An amperometric sensor suitable for determining the concentration of hydrogen peroxide in a sample, said sensor comprising a ferricyanide compound bound to a polymer, which ferricyanide, in reduced form, functions as a mediator selective for hydrogen peroxide, wherein the ferricyanide compound is a ferricyanide compound having a solubility of from 2000 mg/L to 20,000 mg/L in pure water.

13. A sensor according to claim 12, wherein the polymer is a polyacrylamide.

14. A sensor according to claim 12, further comprising an enzyme which is capable of reacting with an analyte in the sample to produce hydrogen peroxide.

15. A sensor according to claim 14, wherein the analyte is glucose and the enzyme is glucose oxidase.

16. A sensor according to claim 12, wherein the ferricyanide compound is of general formula:

$$X_3Fe(CN)_6$$

in which the groups X are the same or different and at least one X is a non-metallic ion.

17. A sensor according to claim 16, in which each X is a quaternary ammonium ion of formula $(R^1)(R^2)(R^3)(R^4)N^+$ in which $R^1$ to $R^4$ are the same or different alkyl groups containing from 1 to 20 carbon atoms, provided that at least one of $R^1$ to $R^4$ contains at least 4 carbon atoms.

18. A sensor according to claim 17, wherein the ferricyanide compound is tetrahexylammonium ferricyanide, tetrakisdecylammonium ferricyanide, tetradecyltrimethylammonium ferricyanide, hexadecyltrimethylammonium ferricyanide or trimethyhexylammonium ferricyanide.

19. A sensor according to claim 16, wherein each X is a phosphonium ion of formula $(R^5)(R^6)(R^7)(R^8)P^+$ in which $R^5$ to $R^8$ are the same or different alkyl groups containing from 1 to 20 carbon atoms, provided that at least one group $R^5$ to $R^8$ contains at least 4 carbon atoms.

20. A sensor according to claim 16, wherein each X is a nitrogen-containing heterocylic cation.

21. A sensor according to claim 20, wherein each X is a pyridinium ion.

22. A sensor according to claim 12, wherein the ferricyanide compound is bound to the polymer via one of groups $R^1$ to $R^4$ of a quaternary ammonium ion of formula $$(R^1)(R^2)(R^3)(R^4)N^+$$

or via one of groups $R^5$ to $R^8$ of a quaternary phosphonimum ion of formula $$(R^5)(R^6)(R^7)(R^8)P^+$$

or via a nitrogen-containing heterocyclic cation.

23. A cartridge for an amperometric sensor suitable for measuring hydrogen peroxide in a sample, which cartridge comprises a ferricyanide compound as defined in claim 12.

24. A cartridge to claim 23, further comprising an enzyme which is capable of reacting with an analyte in the sample to produce hydrogen peroxide.

25. A cartridge according to claim 24, wherein the enzyme is glucose oxidase.

* * * * *